United States Patent [19]

Demoulin et al.

[11] Patent Number: 4,688,938
[45] Date of Patent: Aug. 25, 1987

[54] METHOD AND APPARATUS FOR DETERMINING THE CONTACT ANGLE OF A DROP OF LIQUID PLACED ON A SOLID OR LIQUID HORIZONTAL SUBSTRATE

[75] Inventors: Catherine A. Demoulin, Sceaux; Dominique Ausserré, Le Plessis Robinson; Francis Rondelez, Antony, all of France

[73] Assignee: Centre National de la Recherche Scientifique (C.N.R.S.), Paris, France

[21] Appl. No.: 804,440

[22] Filed: Dec. 4, 1985

[51] Int. Cl.$^4$ .............................................. G01B 11/26
[52] U.S. Cl. ..................... 356/154; 356/138
[58] Field of Search .................. 356/138, 154; 73/64.4

[56] References Cited

U.S. PATENT DOCUMENTS 3,535,043  12/1968  Hong ..................................... 73/64.4

FOREIGN PATENT DOCUMENTS 2053390  10/1970  Fed. Rep. of Germany ....... 73/64.4
6214443  10/1984  Netherlands ........................ 73/64.4

OTHER PUBLICATIONS

"Apparatus for Measuring the Contact Angles at Crystal-Solution-Vapor Interfaces", McLachlan, Jr. et al, *Rev. Sci. Instruments*, vol. 46, #1, 1/1975, pp. 80-83.

"A New Method of Determining the Contact Angle Made by a Sessile Drop Upon a Horizontal Angle (Sessile Drop Contact Angle), Ryley, *Journal of Colloid and Interface Science*, vol. Sq, #2, Apr. 1972, pp. 243-251.

Primary Examiner—R. A. Rosenberger
Assistant Examiner—Crystal D. Cooper
Attorney, Agent, or Firm—Pollock, Vande Sande & Priddy

[57] ABSTRACT

A support (56) is suitable for holding a substrate (10) horizontal, said substrate having a drop of liquid placed thereon. A source of light (74) associated with a collimator (78) forms a primary beam of parallel light which is directed perpendicularly (86) to the substrate. A receiver surface (126, 128) having a known geometry and placed in a known position relative to the substrate intercepts a secondary beam (124) produced by interaction between the primary beam and the drop and the substrate. The value of the contact angle between the drop and the substrate may be deduced from the illuminated zone on said receiver surface.

26 Claims, 12 Drawing Figures

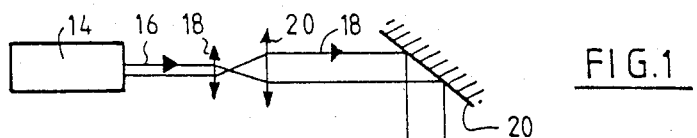
FIG.1
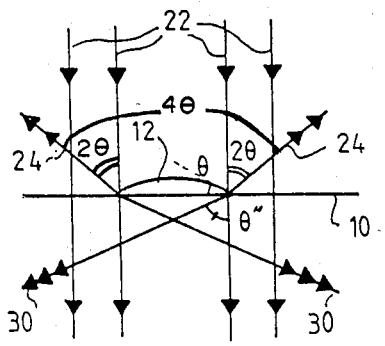
FIG.2
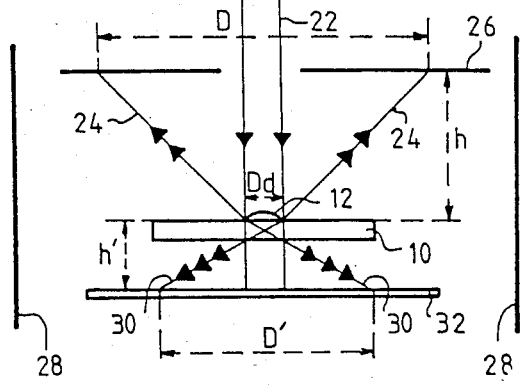
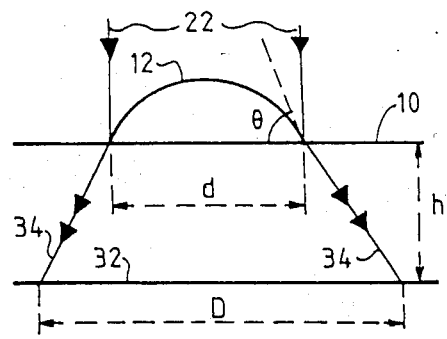
FIG.3
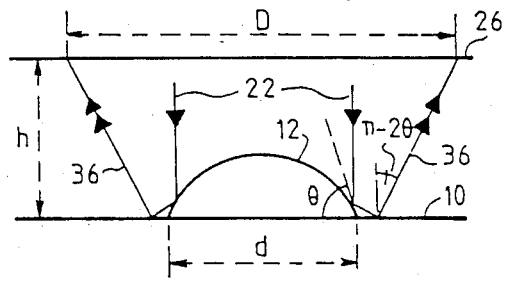
FIG.4
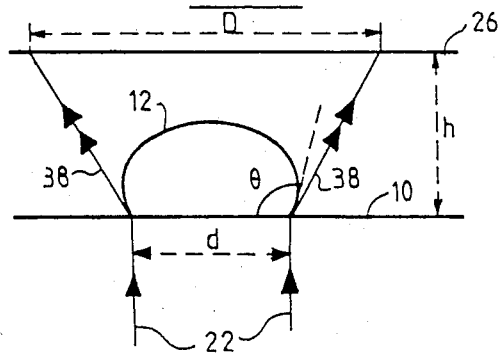
FIG.5
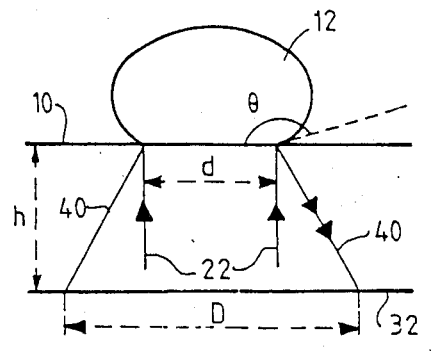
FIG.6

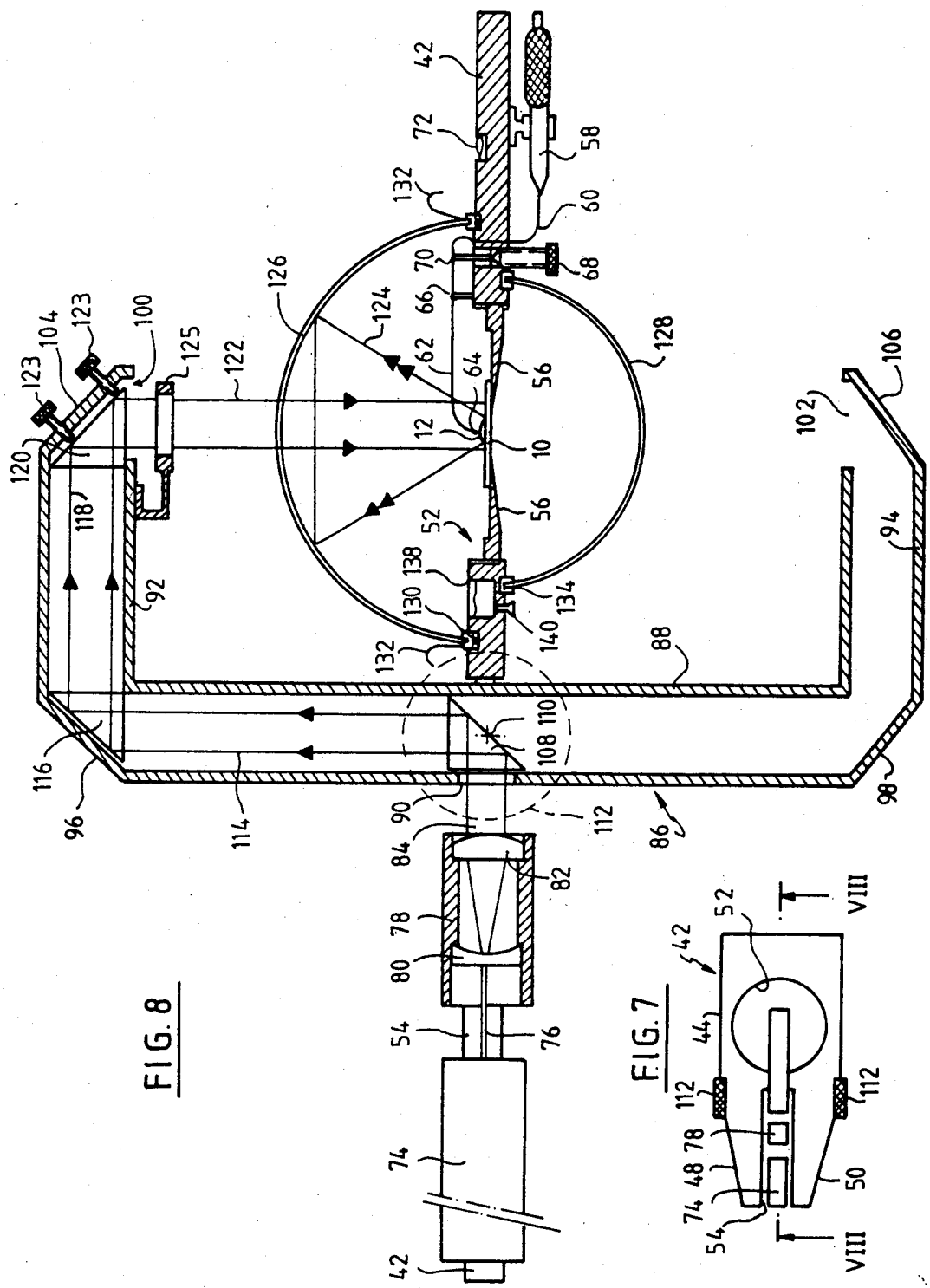

METHOD AND APPARATUS FOR DETERMINING THE CONTACT ANGLE OF A DROP OF LIQUID PLACED ON A SOLID OR LIQUID HORIZONTAL SUBSTRATE

The present invention relates to a method of determining the contact angle which occurs between a drop of liquid and a horizontal substrate which may be solid or liquid on which the drop is placed, the invention also relates to apparatus for performing the method.

BACKGROUND OF THE INVENTION

Contact angle measurements are commonly used to characterize the surface properties of solid or liquid materials. The value of the contact angle between the drop of liquid and the solid or liquid substrate on which the drop rests depends on the forces occurring at the liquid-solid or liquid-liquid interface.

These measurements are applicable not only to liquid substrates for measuring the interface between two liquids, but also with solid substrates for measuring their interface properties, and consequently for measuring their wetting properties.

If perfect and complete wetting takes place, the drop of liquid spreads out over the substrate and the contact angle is zero, whereas if wetting is only partial, the resulting contact angle lies in the range 0° to 180°.

A drop of liquid water surrounded by its vapor may be taken as an example. The drop is placed on a solid substrate and the contact angle $\theta$ on the boundary line between the three phases, i.e. on the triple line, has a single value for smooth homogeneous and isotropic substrate surfaces. This value is related by Young's equation:

$$\gamma_{SV} - \gamma_{SL} = \gamma_{LV} \cos \theta$$

to the free energy $\gamma_{SV}$ at the solid-vapor interface, to the free energy $\gamma_{SL}$ at the solid-liquid interface, and to the tension $\gamma_{LV}$ at the liquid-vapor interface. Zisman emphasized the concept of a critical surface tension for wetting, $\gamma_C$, which is a characteristic of each solid surface. Thus, glass and metals are examples of high energy surfaces over which most liquids spread spontaneously, with the angle $\theta$ tending to zero. In contrast, plastic materials such as tetrafluoroethylene are typical low energy surfaces such that liquids placed on these surfaces remain in the form of drops having finite contact angles so long as $\gamma_C$ is less than $\gamma_{LV}$.

Measurements of these contact angles are used not only for fundamental or applied research, but also in industry for performing routine tests on the surface states of certain materials.

Such measurements are of interest to very many enterprises engaged in a wide range of activities.

For example, enterprises which perform surface state tests on different kinds of material are concerned, in particular the surface states of the following materials are commonly tested: plastic and polymer films; wetting agents and detergents; textiles; inks; glues; composite materials; and special materials such as those used in the biomedical field for contact lenses, dentistry, etc. Another activity which is closely concerned with the surface state of material is depositing thin layers on a substrate for modifying its surface properties, for example depositing a thin layer of tetrafluoroethylene on metal drums for use in offset printing. Other industries are also concerned, for example the oil industry.

At present there are several experimental procedures for measuring contact angles.

Most of these procedures are based on observing a drop placed on a substrate, thus having the advantage of requiring very small quantities of liquid and very small areas of substrate surface, e.g. only a few square millimeters.

In the most widely used procedures, a "silhouette" image of the drop is projected and the drop angle is measured point by point using a telescope and a protractor, which requires a tangent to be estimated by eye. Such procedures are not very reproducible, and a reproducibility of less than ±2° is commonly observed when comparing readings obtained on successive drops or on several different projection views of the same drop.

This lack of reproducibility is made worse by local roughness or lack of uniformity on the solid substrate being used. Given that this problem is inherent to the substrate itself, it will always be present however much care is taken by the experimenter. The only way of reducing dispersion in the results is thus to take the average of a large number of individual measurements, which naturally constitutes a particularly boring and difficult task.

In another known method, interference fringes are created in a liquid wedge formed at the edge of the drop and the contact angle is deduced from the fringe spacing. However, this method is applicable only to determining very small contact angles.

Another measuring procedure consists in autocollimating light very locally on the edge of the drop by means of a beam of light whose angle of incidence relative to the substrate is varied. The intensity of the beam reflected by the drop is observed in order to detect the moment when the beam is extinguished. The position of the incident beam angle can then be used to immediately deduce the contact angle between the drop and the substrate. The drawback with this method, as with the preceding methods is that it requires the measurement to be performed on a particular portion of the drop, thereby leading to poor measurement reproducibility.

Preferred implementations of the present invention avoid the above-mentioned drawbacks since the contact angle between a drop which is placed or "sessile" on the substrate is determined simultaneously over the entire periphery of the drop.

Contact angles can then be determined quickly and accurately, with a typical accuracy of 0.1° rather than 1° to 2° as applicable to the prior arts methods.

The method also provides objective measurement in that it does not require a tangent to the drop to be estimated by eye at the point of contact, thereby avoiding possible variations from one observer to another.

The method in accordance with the invention does not require an optical microscope to be used as is generally the case with prior art methods, it enables badly formed drops to be visually detected immediately, which is generally impossible in prior art methods and constitutes yet another source of erroneous measurements.

The method in accordance with the invention also constitutes an immediate test for substrate uniformity on the basis of the shape of a drop (drop asymmetry, or irregular contour).

Further, the method in accordance with the invention is capable of being automated so that measurements are performed continuously, given that the measurement is particularly simple to implement, as will be seen from the description below.

SUMMARY OF THE INVENTION

The present invention provides a method of determining the contact angle of a drop of liquid placed on a horizontal substrate which may be solid or liquid, the method comprising the following steps:

(a) directing a parallel primary light beam perpendicularly to the surface to illuminate a zone which includes the interface between the periphery of the drop and the substrate, said primary beam interacting with the drop and the substrate to produce at least one secondary beam;

(b) measuring the extent of the illumination transition which occurs in the secondary beam and corresponds to the periphery of the drop, said measurements being performed over at least one receiver surface which intercepts said secondary beam, the position and the geometry of the receiver surface relative to the substrate being known;

(c) thereby enabling the contact angle to be determined from said measurement and from said known position and geometry of said receiver surface.

In a first implementation of the invention, the secondary beam is produced by the primary beam interacting with the drop and the substrate, with the drop acting as a convex mirror.

In a first implementation of the invention, the primary beam may be directed to the face of the substrate on which the drop is placed, or else it may be directed towards the opposite face of the substrate from the face on which the drop is placed, in which case the substrate must be transparent.

When the primary beam is directed to the face of a substrate on which the drop is placed, the secondary beam may be produced in three different ways depending on the range of contact angles and on the nature of the substrate.

In a first variant, the secondary beam is produced by simple reflection of the primary beam on the convex surface of the drop, with the nature of the substrate then being immaterial, and thus variant is suitable for determining contact angles lying in the range 0° to 45°.

In a second variant, the secondary beam is produced by the primary beam being reflected on the convex surface of the drop, and then transmitted through the substrate which must be transparent, thereby enabling contact angles to be determined when they lie in the range 45° to 90°.

In a third variant, the secondary beam is produced by reflection of the primary beam on the convex surface of the drop, followed by reflection on the substrate, in which case the substrate must act like a plane mirror, and this enables contact angles to be determined lying in the range 45° to 90°.

In the first implementation, and using a transparent substrate with the primary beam being directed to the opposite face of the substrate to the face on which the drop is placed, it is possible to determine contact angles lying in the range 90° to 180°.

In accordance with a second embodiment of the invention, the secondary beam is produced by interaction of the primary beam with the drop and the substrate, the drop acting as a plano-convex lens and the substrate being transparent, and this enables contact angles to be determined lying in the range 0° to 90°.

The receiver surface used for performing the method in accordance with the invention may, in particular, be a plane surface disposed parallel to the substrate, or a generally cylindrical surface whose axis runs perpendicularly to the substrate and passes through the center of the drop, or else a surface in the form of a hemispherical cap centered on the drop, and having a horizontal equator line. A receiver surface in the form of a hemispherical cap is particularly advantageous since it enables the contact angle to be read directly, providing the hemispherical cap is provided with suitable angle graduations.

The receiver surface may also constitute a part of an automatic detector device, e.g. a video camera connected to a computer, or an optoelectronic detector of the photoresistance type, and if possible with a highly nonlinear response.

The invention also provides apparatus for performing the method, said apparatus comprising a support suitable for holding a substrate horizontally, a source of light, means for forming a primary parallel light beam from said source, means for directing said beam perpendicularly to the substrate, and at least one receiver surface of known geometry and located in a position relative to the substrate which is also known, said receiver surface serving to intercept the secondary beam produced by interaction of the primary beam with the drop and the substrate.

The means used in the apparatus for directing the primary beam perpendicularly to the substrate are advantageously constituted by pointing means for directing the primary beam either to the face of a substrate on which the drop is placed, or else in the opposite direction.

BRIEF DESCRIPTION OF THE DRAWINGS

Implementations of the invention are described by way of example with reference to the accompanying drawings, in which:

FIG. 1 is a diagram of apparatus for performing the method in accordance with the invention, in order to determine the contact angle of a drop of liquid placed on a substrate;

FIG. 2 is a detail of FIG. 1 showing more particularly the disposition of the primary beam and of the secondary beams as reflected and refracted by the drop of liquid;

FIGS. 3 to 6 are similar to FIG. 2 showing the disposition of the primary beam and of the secondary beam for various different modes and variants of implementation of the method;

FIG. 7 is a plane view of measuring apparatus in accordance with the invention;

FIG. 8 is a section view taken on a line VIII—VIII of FIG. 7 and drawn to a larger scale;

MORE DETAILED DESCRIPTION

Figure 9:
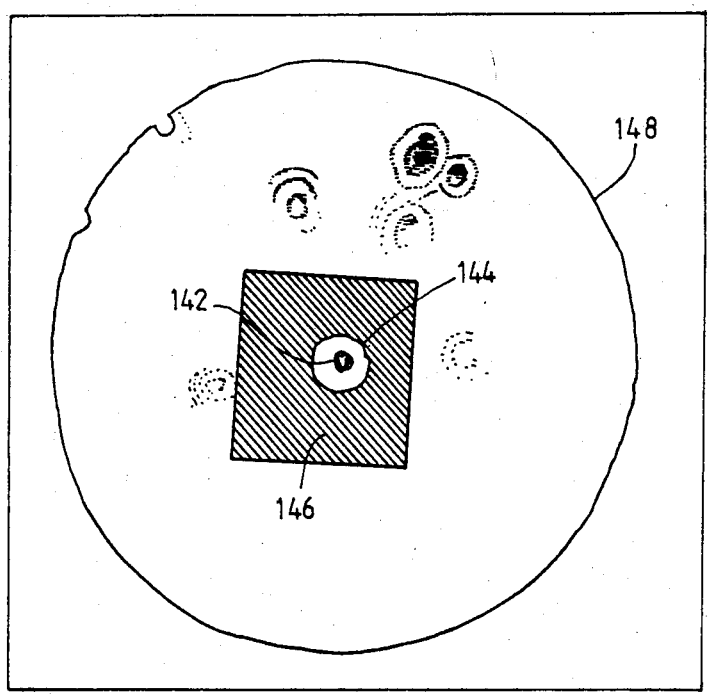
FIG. 9 shows the refracted "image" obtained using apparatus in accordance with the invention on a plane receiver surface such as a photographic plate.

FIG. 1 shows a solid horizontal substrate constituted by a plate of glass 10 which may, for example, be a microscope slide. The top face of the plate 10 has a drop of liquid 12 placed thereon, which drop has a contact angle $\theta$ with the substrate (see FIG. 2). As can be seen in FIG. 1, a source of light 14 e.g. a source suitable for emitting laser radiation, emits a beam of light which is parallel and horizontal and whose diameter is expanded by means of two lenses 18 and 20 disposed in an afocal configuration. The diameter of the beam 16 is increased in this manner in order to form a beam 18 which is directed towards a mirror 20 disposed at an angle of 45° relative to the horizontal in such a manner as to emit a primary beam 22 of parallel light towards the substrate 10. The diameter and the orientation of this beam of light must be suitable for illuminating a zone which includes the interface between the periphery of the drop and the substrate. In practice, the beam 22 is arranged to be vertically directed on the center of the drop and to have a diameter which is greater than the diameter $D_d$ of the drop.

By way of example, the source 14 may be a helium-neon laser source operating at a wave length of 632.8 nanometers and suitable for emitting a laser beam having a diameter of 1.5 mm. The beam may then be expanded to a diameter of 1 centimeter, for example, i.e. the beam is expanded sufficiently to ensure that it can completely cover a drop whose contact angle on the substrate is to be measured.

As described below with reference to FIGS. 7 and 8, it is also advantageous to provide means for enabling the primary beam 22 to be directed towards the substrate from the opposite face of the substrate from the face on which the drop is placed. In this manner, it is possible to illuminate the drop from below, as explained below.

The primary beam 22 interacts with the drop 12 and the substrate 10 in order to produce at least one secondary beam.

The surface of the drop acts as a convex mirror which reflects a secondary beam 24 constituted by a tone of light whose aperture angle is equal to $4\theta$, where the contact angle at the periphery of the drop is assumed to be constant (see FIG. 2). FIG. 2 shows the half aperture angle of beam (24) being equal to $2\theta$ which, in turn, means that the total aperture angle is equal to $4\theta''$. The reflected image is intersected on a receiver surface of known geometry which is placed in a known position relative to the substrate. This makes it possible to measure the extent of the transition in the illumination presented by the secondary beam 24 in correspondance with the periphery of the drop 12.

As shown in FIG. 1, the image is intercepted on a receiver surface constituted by a screen 26 which is disposed horizontally at a distance h from the substrate. Thus, a bright spot is obtained on the screen, which spot is generally circular having a diameter D. It can easily be shown that the diameter D is related to $\theta$ by the relationship:

$\tan 2\theta = (D - D_d)/2h$

Thus, given the value of h and after measuring the values of $D_d$ and of D, it is possible to obtain the value of $\theta$ as required.

In a variant, the secondary beam 24 may be intercepted on a generally cylindrical surface 28 whose axis is perpendicular to the substrate and passes through the center of the drop.

In another variant, described below, the receiver surface may be constituted by a spherical cap with the center of the sphere coinciding with the center of the drop.

The secondary beam 24 is produced by a single reflection of the primary beam 22 on the convex surface of the drop which acts as a mirror, and in this case the nature of the substrate is immaterial. This can be used for measuring contact angles lying in the range 0° to 45°.

In addition to constituting a mirror, the drop 12 can also act as a plano-convex lens providing the substrate 10 is transparent to the beam 22. In this case, a refracted beam 30 may be produced which is intercepted on a receiver surface 32, which may be constituted by a photographic plate, for example, disposed horizontally at a distance h' relative to the face of the substrate 10 on which the drop is placed. It should be observed that the surface 32 must be disposed beneath the substrate 10 and that a generally circular spot is similarly observed on the surface 32, this time having an outside diameter D' (see FIG. 1).

If the refractive index n of the liquid constituting the drop is known, then D' is related to the value h' and the contact angle $\theta$ by the following relationships:

$\tan \theta = (\sin \theta'')/((n^2 - \sin^2\theta'')^{\frac{1}{2}} - 1)$
$\tan \theta'' = (D' + D_d)/2h'$ where $\theta''$ is the refracted angle at the top of the drop (see FIG. 2). The secondary beam 30 may also be intercepted on the cylindrical surface 28 or on a receiver surface of the spherical cap type.

In the above-mentioned variant, where the secondary beam 30 is refracted by the drop, contact angles can be measured lying in the range 0° to 90°.

In the variant shown in FIG. 3, the primary beam 22 is directed to the face of the substrate 10 on which the drop is placed. The secondary beam 34 is produced by a first reflection of the primary beam 22 on the convex surface of the drop, followed by transmission through the substrate 10, which is transparent. This can be used for measuring contact angles in the range 45° to 90°. In this case, the receiver surface 32 must obviously be placed beneath the substrate 10.

It can be shown, that the value $\theta$ may be deduced from the relationship $\tan 2\theta = -(D-d)/2h$, and consequently that $2\theta = \pi - \arc \tan ((D-d)/2h)$. In this relationship, D designates the diameter of the image on the receiver surface, d designates the diameter of the drop, and h designates the distance between the substrate and the receiver surface.

In the variant embodiment shown in FIG. 4, the primary beam 22 is again directed to the face of the substrate 10 on which the drop is placed. The secondary beam 36 is produced in this case by a first reflection of the primary beam on the convex surface of the drop, followed by a second reflection on the substrate 10, with the substrate acting as a plane mirror, thereby enabling contact angles to be determined in the range 45° to 90°. In this variant, the receiver surface 26 must be disposed above the substrate 10.

The value $\theta$ is obtained from the relationship $2\theta = \pi - \arctan((D-d)/2h)$, where D, d, and h are defined as before.

In the FIG. 5 variant, the substrate 10 is transparent and the primary beam is directed to the face of the substrate opposite the face on which the drop is placed. In the FIG. 5 case where the contact angle $\theta$ lies between 90° and 135°, the secondary beam 38 is reflected into the region of space above the substrate 10. A receiver surface 26 should thus be disposed in this region of space. The value of $\theta$ is deduced from the relationship $2\theta = \pi + \arctan -((D-d)/2h)$, where D, d and h are defined as above.

In the FIG. 6 embodiment, which is very close to the FIG. 5 embodiment since the substrate is transparent and the primary beam is directed towards the face of the substrate opposite to that on which the drop is placed, contact angles are measured lying in the range 135° to 180°. However, in this particular case, the secondary beam 40 is reflected into the region below the substrate 10. It is thus necessary to put the receiver surface 32 below the substrate. The value $\theta$ is obtained in this case by the relationship $2\theta = 2\pi - \arctan((D-d)/2h)$, where D, d and h are defined as before. Thus, by using the arrangement shown in FIG. 5 or in FIG. 6, it is possible to determine contact angles lying in the range 90° to 180°.

The above-mentioned relationships giving the values of $\theta$ are established for plane receiver surfaces of the screen type. However, in the various embodiments described with reference to FIGS. 3 to 6, the receiver surfaces could be made in the various ways described with reference to FIGS. 1 and 2.

Reference is now made to FIGS. 7 and 8 in order to describe apparatus according to a preferred embodiment of the invention.

This apparatus comprises a frame 42 which is intended to be placed horizontally by means of adjustable feet (not shown) fixed to the frame. The frame 42 is delimited by two parallel sides 44 and 46 which continue along respective tapering non-parallel sides 48 and 50 in order to form a narrow portion (see FIG. 7). The frame 42 thus constitutes a thick table in which an opening 52 is provided which is generally circular in shape, said opening lying between the parallel sides 44 and 46 and having an open longitudinal slot 54 extending between the tapering sides 48 and 50 (see FIG. 7). Inside the opening 52 there is a sample holder 56 of adjustable height for receiving a substrate having a drop of liquid 12 on the top surface thereof. In order to place the drop of liquid on the substrate a microsyringe 58 is used which is fixed beneath the frame 42 and which is connected via a flexible pipe 60 to one end of a hollow needle 62 whose other end 64 is curved over to place the drop 12 on the substrate 10. The needle 62 is pivotally mounted about a horizontal axis 66 and its position is adjustable by means of a knurled knob 68 which alters the vertical position of an abutment 70 which co-operates with the needle 62 in the vicinity of its end which is connected to the flexible pipe 60. The frame 42 may be levelled by means of a bubble level 72 disposed in a hollow in the top face of the frame 42.

A light source 114 is disposed in the slot 54, and may be a helium-neon laser suitable for emitting a horizontally-directed beam 76. The diameter of the beam 76 is increased by means of a beam enlarger 78 which comprises two lenses 80 and 82 disposed in an afocal configuration. Thus, a parallel output beam 84 is provided. The beam 84 may be deflected in two different directions by means of an optical device given an overall reference 86. This optical device comprises a vertical tube 88 of square section having an opening 90 in its middle portion for receiving the primary beam 84. The tube 88 has a horizontal tube 92 fixed to the top thereof and a horizontal tube 94 fixed to the bottom thereof with both horizontal tubes being square in section. The connection between the tube 88 and the tube 92 and between the tube 88 and the tube 94 is provided in each case by a respective plane mirror 96 or 98 disposed at 45°. The tube 92 defines a horizontal opening 100 disposed above the substrate and aligned with the region of the substrate which is to receive a drop. Similarly, the tube 94 defines a horizontal opening 102 which is disposed below and in alignment with said region of the substrate. Adjacent to the openings 100 and 102, the tubes 92 and 94 are closed by inclined plates 104 and 106 which are disposed at 45°. A prism or a mirror 108 is placed inside the vertical tube 88 opposite to its opening 90, said prism or mirror being rotatable about a horizontal axis 110 by means of handles 112 so as to provide a beam 114 which may be directed upwardly or downwardly. In the configuration shown in FIG. 2, the beam 114 is shown directed upwardly. The beam 114 is deflected through 90° by a prism 116 disposed at the intersection between the tubes 88 and 92 so as to emit a horizontal beam 118 which is again deflected by another prism 120. The prism 120 is disposed inside the tube 92 and opposite to the opening 100 so as to emit a primary beam of parallel light 122 which is directed vertically towards the drop 12 on the substrate 10. The verticality of the beam 122 may be adjusted by means of screws 123, or the like passing through a sloping plate 104 and acting on the prism support in order to modify its orientation.

Naturally, two other prisms analogous to the prisms 116 and 120 are disposed in the corresponding intersection between the tube 88 and the tube 94 and in the tube 94 opposite to the opening 102.

At the output from the prism 120, the primary beam 122 may optionally pass through a diaphragm 125 prior to be directed to the drop on the substrate.

The substrate 10 may be a plate, for example a glass plate having a plane polished surface for receiving a drop of liquid. The substrate may also be some other form of solid substrate, e.g. a film, or it may a liquid substrate, such as a film of liquid which is not miscible with the drop-constituting liquid. In the following description, the substrate is assumed to be a glass plate.

In the embodiment shown in FIG. 8, the primary beam 122 is reflected by the convex surface of the drop 12 which acts as mirror to return a secondary beam 124 which is to be intercepted on a receiver surface.

A first receiver 126 in the form of a hemispherical cap centered on the drop 12 is disposed above the substrate 42 so that its equator line is horizontal and rests against the frame 42. The position of the substrate is adjusted to bring its top face into the equatorial plane of the hemispherical cap.

A second receiver surface 128 which is likewise shaped like a hemispherical cap centered on the drop is placed in such a manner that its equatorial line is horizontal and presses against the bottom face of the frame 42. The hemispherical receiver surface 116 above the substrate 10 has a larger diameter than the hemispherical receiver surface 128 below the substrate 10, and both receiver surfaces are made of diffusing material and are advantageously graduated in order to provide direct reading of the angular aperture of the, or each secondary beam.

The upper receiver surface 126 is connected in sealed manner to the frame 42 by means of a sealing ring 130 and it may be removed from the frame by means of handles 132.

The lower receiver surface 128 is likewise connected in sealed manner to the frame by means of a sealing ring 134. The lower receiver surface 128 is normally intended to remain fixed on the frame but it can be removed in case of necessity.

These two receiver surfaces 126 and 128 thus define a hermetically sealed enclosure around the drop 12, thereby enabling the drop of liquid to be maintained in equilibrium with its vapor. To this end, a tank 138 is provided for receiving a solvent capable of saturating the atmosphere inside the enclosure and it is received in the thickness of the frame 42 in the annular region lying between the opening 52 and the equator of the upper hemisphere 126. The tank 138 may be emptied via an emptying orifice which is closed by a removable stopper 140.

If necessary, the apparatus may include heater means for raising the temperature of the drop liquid to above ambient temperature. Such heater means are already known in the art and are used in other installations for measuring contact angles.

In a variant embodiment (not shown) the optical device 86 could be constituted simply by a bent arm constituted by the top portion of the tube 88 and by the tube 92, the arm could then be pivotally mounted about a horizontal axis coaxial with the beam 86 and the beam 84, thereby allowing the device to be moved between two different positions, i.e. a position above the frame and a position below the frame.

It may also be observed that the apparatus shown in FIG. 7 and 8 could be equipped with different kinds of receiver surface, in particular it could be equipped with plane screen or cylindrical screen type receiver surfaces as described above with reference to FIG. 1. The receiver surfaces could also constitute a portion of an automatic detector device, as mentioned above.

Figure 10:
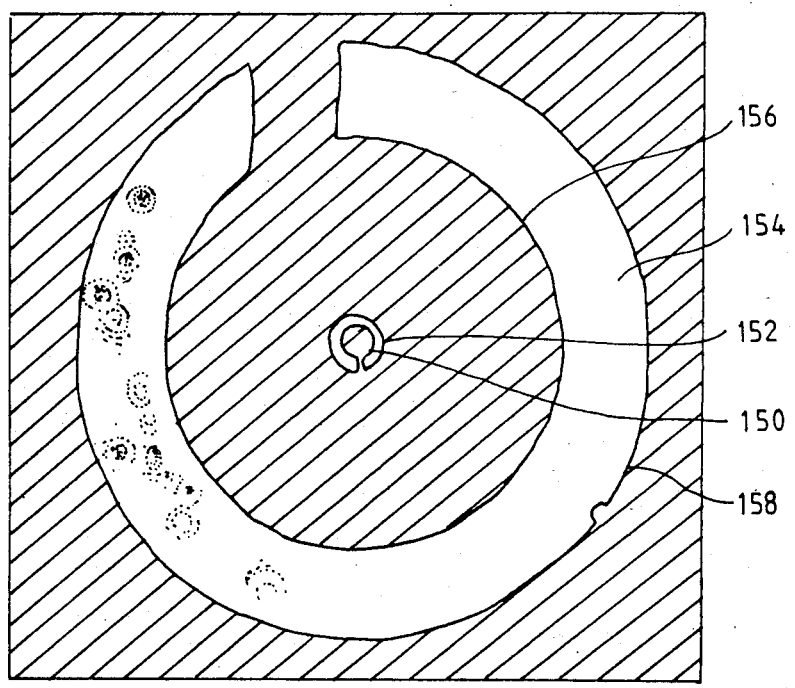
FIG. 10 shows a refracted "image" obtained under the same conditions as the "image" of FIG. 9, but in which the drop-placing needle has remained in place during the measurement.

The images shown in FIGS. 9 and 10 are two examples of refracted images obtained using a device as shown in FIG. 8, but using a plane screen of the photographic plate type, analogous to the screen 32 shown in FIG. 1, i.e. disposed below the substrate and parallel thereto.

FIG. 9 corresponds to the needle 62 being taken away and the drop 12 taking up the shape of a non-disturbed portion of a sphere. Observing this image and going outwards from its center, the following features may be seen:

a dark circle 142 corresponding to the shadow projected by the drop, thus giving an image to the same scale as the drop;

a bright circle 144 corresponding to the impact of the primary beam of laser light on the photographic plate, it can be seen that in this particular case the diameter of the beam is about three times the diameter of the drop, with the diameter of the beam being adjustable by means of the diaphragm 125;

a square 146 delimiting the edges of a neutral density filter for avoiding overexposure of the film by the directly-transmitted laser beam; and a refracted and expanded "image" 148 of the sessile drop. This image may be used to directly measure the outside diameter D' in order to calculate the angle $\theta''$ and thus the contact angle $\theta$ (see FIGS. 1 and 2). The fringes which may be observed are due to defraction by the edges of the drop and are independent of the real contact angle along the three phase line. These fringes must not be confused with the interference fringes which occur due to the combination of two reflections, i.e. to the solid-liquid interface and to the liquid-vapor interface. These fringes are easily eliminated by using parallel white light which slightly increases the accuracy with which D' may be determined. However, the use of a source of white light requires a heat absorbing filter to be used.

FIG. 10 corresponds to the case where the needle 62 remains in contact with the sessile drop. Contact between the point of the needle and the drop deforms the otherwise spherical nature of the drop. The liquid wets the needle material (stainless steel) and its contact angle with the needle is practically zero. Also, the shape of the drop in the region where it comes into contact with the solid substrate is governed by the energies of the three interfaces and not by the shape of the liquid-vapor interface at a distance from the three phase line.

It thus appears that the liquid region adjacent to the line of contact with the solid remains unaffected by the surface deformation caused by the point of the needle. The final result is that measurements can be made while the needle is still in place. However, it should be observed that when using this geometry, the angle of incidence between the primary beam (which is vertical), and the form to the air-liquid interface varies continuously with the position of the beam. It starts from the real value $\theta$ of the contact angle at the three phase line. It then drops towards a non-zero value at a point of inflection whose position depends on the degree of disturbance induced by the needle. After passing this point it increases again in order to reach 90° at the tip of the needle.

The properties of the refracted beam follow this variation.

The angle of refraction takes a value $\theta''$ (which is related to $\theta$) at the three phase line, it passes through a minimum value or point of inflection and then increases again as it approaches the needle tip. This explains the refracted image observed in FIG. 10.

Outside the shadow 150 of the drop, and the direct projection 152 of the primary laser beam on the photographic plate, the refracted light is concentrated to form a halo 154 which is delimited by a sharp boundary 156 on the inside and by a diffuse line 158 on the outside.

It is easy to understand, from optical and geometrical considerations that the sharp boundary corresponds to the point of inflection in the drop's profile, and that the diffuse boundary corresponds to the refracted angle $\theta''$ along the periphery of the drop.

A comparison between FIGS. 9 and 10 shows that the position of the diffuse line as indicated by the diameter D' is exactly the same as that observed in the absence of any contact between the drop and the needle. This confirms the hypothesis that the contact angle $\theta$ is not modified by the presence of the needle. As a consequence, measurements may be performed equally well with the needle removed from the drop it had been used to put into position, or leaving the needle in contact with the drop.

In FIGS. 9 and 10 it will be observed that the drop images are practically circular. Characteristically, the fluctuations in drop diameter do not exceed ±2%.

However, cases may arise where the image is much less circular. One of the advantages of the invention is that it provides "images" which are greatly enlarged and thus make it much easier to detect ill-formed drops which would otherwise have escaped the experimenter's attention. This makes it possible to reject a priori "images" which could lead to erroneous measurements.

Figure 11:
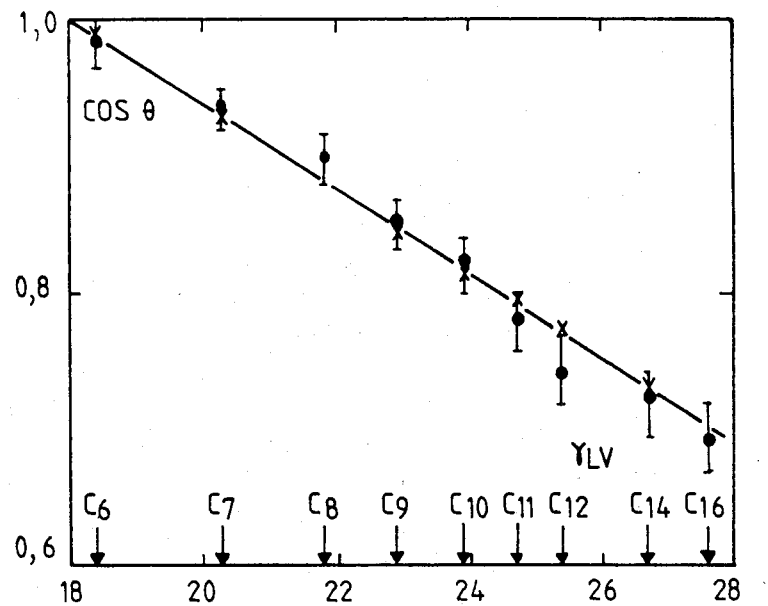
FIG. 11 is a graph showing how the cosine of the contact angle $\theta$ varied as a function of the liquid vapor interface tension for a series of n-alcanes at ambient temperature, said graph being obtained from a series of measurements performed in accordance with the invention on a polytetrafluoroethylene substrate.
Figure 12:
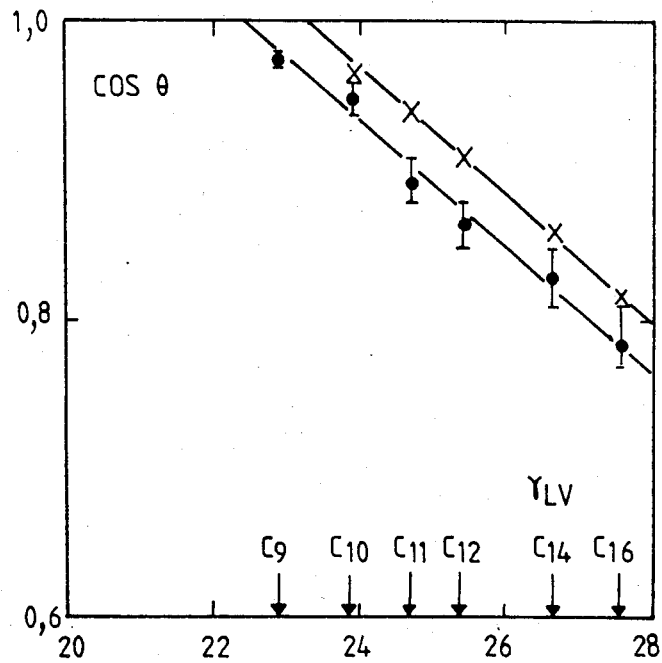
FIG. 12 is a graph obtained under the same conditions as the FIG. 11 graph, but using a substrate constituted by a plate of borosilicate glass covered with a monolayer of hexadecanol.

Reference is now made to FIGS. 11 and 12 which combine the results of contact angle measurements obtained using the method of the invention on a series of liquid n-alcanes (hexane to hexadecane) disposed on plates of hydrophobic glass and/or on plates of polytetrafluroethylene.

The purest available commercial grades of alcanes were used for these experiments (purity better than 99%) and no further purification was performed. Commercially available glass microscope slides were used as the substrates. After carefully cleaning the slides in detergent and sulfochromic acid, and after rinsing, these slides were covered with a monolayer of n-hexadecanol which had previously been recrystalized in ethyl acetate. Alcohols react with the acid surface hydroxyl groups on the silica to form covalent Si—O—C—X bonds, thereby releasing water. These bonds are completely stable both thermally and chemically. The hydrophilic surface of the silica is thus replaced by an outer surface with a high density of methyl groups, which surface is hydrophobic. This is readily demonstrated by the high contact angle which occurs when drops of water are placed on the surface.

Commercially-available plates of polytetrafluoroethylene were also used as substrates. The surface finish of these plates was progressively improved by using finer and finer glass paper. However, the finish was still not good enough to guarantee good surface conditions. Consequently the surface finishing operation was completed by heating the plastic material to 200° C. for a period of several hours while compressing the plastic between two high quality optically plane surfaces.

In these experiments, the drops of liquid were placed on the plates by using hypodermic needles connected to a micro-syringe as shown with reference to FIG. 8. Solvent evaporation was minimized by enclosing the assembly in a sealed enclosure filled with saturated solvent vapor. Photographs of reflected or refracted images were taken after a time interval of 10 to 20 seconds in order to allow the drop to reach mechanical equilibrium on its substrate.

The measurements performed on the n-alcane series were generally started using lower numbered equivalents since they are more volatile and easier to eliminate. Between each series of experiments on a given alcane and the next, the substrate, the syringe, and the needle were carefully cleaned using acetone or toluene. For each of these liquids, the measured contact angle was the average of at least ten independent measurements on successive drops. With such a method, the absolute accuracy (including reproducability) was ±0.25° over the tested range of angles. The data obtained with different alcanes is shown in FIGS. 11 and 12 which correspond respectively to using a polytetrafluoroethylene (PTFE) substrate and a hydrophobic glass substrate.

With reference to FIG. 11, the cosine of the contact angle $\theta$ is plotted as a function of the liquid-vapor interface tension $\gamma_{LV}$ of the pure liquid. These measurements were performed with a series of n-alcanes at ambient temperature (22° C.). On the graph $C_6$ represents hexane, $C_{16}$ represents hexadecane, etc. The solid surface was a plate of polytetrafluoroethylene polished in the above-described manner. The crosses correspond to measurements performed in accordance with the invention, whereas the black dots represent prior data, obtained with error limits of ±2°.

A least squares fit gives:

$$\cos \theta = -0.031\gamma_{LV} + 1.555$$

From which it can be deduced that the value of $\gamma_{LV}$ for which $\cos \theta = 1$ is $18.0 \pm 0.2$ dynes cm$^{-1}$. This value is of particular importance since it defines the minimum surface tension below which a pure liquid spreads out spontaneously, i.e. forms a zero contact angle.

The values obtained in this way agree well with the literature.

With reference to FIG. 12, $\cos \theta$ is plotted as a function of the liquid-vapor interface tension $\gamma_{LV}$, for undecane ($C_{11}$), dodecane, tetradecane ($C_{14}$) and headecane ($C_{16}$) at ambient temperature (20° C.). The crosses correspond to measurements performed in accordance with the invention. When the solid surface is a plate of borosilicate glass covered by a monolayer of hexadecanol, a least squares fit gives:

$$\cos \theta = -0.042\gamma_{LV} + 1.97.$$

From which it can be deduced that the value of $\gamma_{LV}$ for which $\cos \theta = 1$ is $23.3 \pm 0.3$ dynes cm$^{-1}$.

The solid circles on this graph correspond to prior data obtained with error limits of ±2%. The solid surface used was a plate of platinum covered with a monolayer of octadecyl-amine. In both cases, the outermost layer of the monolayers is a dense concentration of methyl groups.

The experimental values obtained using the method in accordance with the invention are in complete agreement with the values found in the literature. These experiments confirm that the method in accordance with the invention is well founded and they also underline the advantages which the method provides, which advantages are mentioned at the beginning of the present description.

In the apparatus described with reference to FIGS. 7 and 8, the sample carrier 56 is provided for a solid substrate such as a glass slide. However, a suitable sample-carrier may be devised for any given kind of solid or liquid substrate, and then fitted to the frame 42, e.g. by means of screws. The apparatus may thus be immediately adapted to a wide range of different kinds of substrate.

Although the present description is given in terms of a receiver surface on which a light "image" is formed, it must be understood that this "image" is not a genuine image of the drop, but is rather a representation or angle chart of the perimeter of the drop. In this respect, it should be observed that detecting possible defects in a drop whose contact angle is being measured, has nothing to do with the size of the representation or angle chart. Even if the representation is reduced to a size comparable to that of the drop, the defect, if any, will always be much more apparent on the chart than when looking at the drop itself.

In other words defects can be detected which are invisible even for an attentive observer using conventional techniques, and indeed, such defects become very obvious using the present invention.

We claim:

1. A method of determining the contact angle of a drop of liquid placed on a horizontal substrate which may be solid or liquid, the method comprising the following steps:
   (a) directing a parallel primary light beam perpendicularly to the surface to illuminate a zone which includes the interface between the periphery of the drop and the substrate, said primary beam interacting with the drop and the substrate to produce at least one secondary beam;
   (b) intercepting said at least one secondary beam with at least one receiver surface to produce a spot corresponding to the periphery of the drop, the position and the geometry of the receiver surface relative to the substrate being known; and measuring the extent of said spot on said receiver surface;
   thereby enabling the contact angle to be determined from said measurement and from said known position and geometry of said receiver surface.

2. A method according to claim 1, wherein the secondary beam is produced by interaction of the primary beam with the drop and the substrate the drop acting as a convex mirror.

3. A method according to claim 2, wherein the primary beam is directed towards the face of the substrate on which the drop is placed.

4. A method according to claim 3, wherein the secondary beam is produced by a single reflection of the primary beam on the convex surface of the drop, thereby enabling contact angles to be determined in the range 0° to 45°.

5. A method according to claim 3, wherein the secondary beam is produced by a first reflection of the primary beam on the convex surface of the drop, followed by transmission through the substrate the substrate being transparent, thereby enabling contact angles to be determined lying in the range 45° to 90°.

6. A method according to claim 3, wherein the secondary beam is produced by a first reflection of the primary beam on the convex surface of the drop, followed by a reflection on the substrate, said substrate acting as a plane mirror, thereby enabling contact angles to be determined lying in the range 45° to 90°.

7. A method according to claim 2, wherein the substrate is transparent and wherein the primary beam is directed towards the face of the substrate opposite to the face on which the drop is placed, thereby enabling contact angles to be determined lying in the range 90° to 180°.

8. A method according to claim 1, wherein the secondary beam is produced by interaction of the primary beam with the drop and the substrate the drop acting as a plano-convex lens and the substrate being transparent, thereby enabling contact angles to be determined lying in the range 0° to 90°.

9. A method according to claim 1, wherein the substrate is a solid substrate, such as a plate or a film, and wherein the substrate has a generally plane surface for receiving the drop of liquid.

10. A method according to claim 1, wherein the substrate is a film of liquid which is not miscible of the drop-constituting liquid.

11. A method according to claim 1, wherein the receiver surface is a plane surface disposed parallel to the substrate.

12. A method according to claim 1, wherein the receiver surface is a generally cylindrical surface whose axis is perpendicular to the substrate and passes through the center of the drop.

13. A method according to claim 1, wherein the receiver surface is in the form of a hemispherical cap centered on the drop, and wherein the equatorial line of the hemisphere is horizontal.

14. A method according to claim 1, wherein the receiver surface is a screen.

15. A method according to claim 1, wherein the receiver surface is a photosensitive surface or a photographic plate.

16. A method according to claim 1, wherein the receiver surface constitutes a portion of an automatic detector device.

17. A method according to claim 1, wherein the primary beam is a laser beam or a beam of white light.

18. A method according to claim 1, wherein the substrate is disposed inside an enclosure where the drop-constituting liquid is in equilibrium with its vapor.

19. Apparatus for performing the method according to claim 1, wherein the apparatus comprises a support suitable for holding a substrate horizontally, a source of light, means for forming a primary parallel light beam from said source, means for directing said beam perpendicularly to the substrate, and at least one receiver surface of known geometry and located in a position relative to the substrate which is also known, said receiver surface serving to intercept the secondary beam produced by interaction of the primary beam with the drop and the substrate.

20. Apparatus according to claim 19, wherein the means for directing the primary beam perpendicularly to the substrate comprise pointing means for directing the primary beam either towards the face of the substrate on which the drop is placed, or else in the opposite direction.

21. Apparatus according to claim 20, wherein said pointing means comprise a first rotatable prism or mirror suitable for receiving a horizontal primary beam and emitting a vertical beam which is directed either upwardly or downwardly, at least one second prism suitable for deflecting the vertical beam through 90° to return it to the horizontal, and at least one third prism suitable for deflecting the horizontal beam to return it to the vertical and to form a vertical beam which is directed towards the substrate.

22. Apparatus according to claim 21, wherein the position of the third prism is adjustable by means of a screw.

23. Apparatus according to claim 19, including at least one plane receiver surface disposed parallel to the substrate.

24. Apparatus according to claim 19, wherein it comprises a receiver surface which is generally cylindrical in shape having its axis directed perpendicularly to the substrate and passing through the center of the drop.

25. Apparatus according to claim 19, including two receiver surfaces each in the shape of a spherical cap, said receiver surfaces being disposed above and below the support respectively and together defining a sealed enclosure surrounding the substrate and the drop of liquid placed thereon.

26. Apparatus according to claim 19, wherein the primary beam is a laser beam or beam of white light.

* * * * *